(12) United States Patent
Major et al.

(10) Patent No.: US 7,906,105 B1
(45) Date of Patent: Mar. 15, 2011

(54) ZINC-ACTIVATED CONTRAST AGENTS

(75) Inventors: Jody L. Major, Chicago, IL (US); Thomas J. Meade, Wilmette, IL (US)

(73) Assignee: Northwestern University, Evanston, IL (US)

( * ) Notice: Subject to any disclaimer, the term of this patent is extended or adjusted under 35 U.S.C. 154(b) by 657 days.

(21) Appl. No.: 11/844,088

(22) Filed: Aug. 23, 2007

Related U.S. Application Data

(60) Provisional application No. 60/839,722, filed on Aug. 23, 2006.

(51) Int. Cl.
*A61B 5/055* (2006.01)
*C07D 225/00* (2006.01)

(52) U.S. Cl. .................... 424/9.363; 540/465

(58) Field of Classification Search .............. None
See application file for complete search history.

(56) References Cited

OTHER PUBLICATIONS

Meade et al. Current Opinion in Neurobiology, 2003, 2003, 13, 597-602.*
Major et al. PNAS, 2007, 104(35), 13881-13886.*
Hanaoka et al. Journal of the Chemical Society, PerkinTransactions 2, 2001, 1840-43.*
Towner et al. (The Journal of Trace Elements in Experimental Medicine, 2004, 17, 161-174.*
Bertini et al., "Nuclear spin relaxation in paramagnetic complexes of S=1: Electron spin relaxation effects," J Chem Phys 1999, 11:5795-5807.
Bloemenbergen et al., "Proton Relaxation Times in Pramagnetic Solutions. Effects of Electron Spin Relaxation ," J Chem Phys 1961, 34:842-850.
Bush, A. I., "The metallobiology of Alzheimer's disease," Trends in Neurosciences 2003, 26:207-214.
Caravan et al., "Gadolinium(III) Chelates as MRI Contrast Agents: Structure, Dynamics, and Applications ," Chem Rev 1999, 99:2293-2352.
Dadabhoy et al., "Long wavelength sensitizers for europium(III) luminescence base on acridone derivatives," J Chem Soc 2002, 2:348-357.

Fredrickson et al., "Is zinc the link between compromises of brain perfusion (excitotoxicity) and Alzheimer's disease?" J Alzheimer's Disease 2005, 8:155-160.
Fredrickson et al., "The Neurobiology of Zinc in Health and Disease," Nature Reviews 2005, 6:449-462.
Hanaoka et al., "Selective sensing of zinc ioins with a novel magnetic resonance imaging contrast agent," J Chem Soc, Perkin Transactions 2 2001, 1840-1843.
Hanaoka et al., "Design and Synthesis of a Novel Magnetic Resonance Imaging Contrast Agent for Selective Sensing of Zinc Ion," Chem Bio 2002, 9:1027-1032.
Hwang, L.-P and Freed, J. H., "Dynamic effects of pair correlation functions on spin relaxation by translational . diffusion in liquids," J Chem Phys 1975, 63(9):4017-4025.
Kikuchi et al., "Zinc sensing for cellular application," Curr Opin Chem Bio 2004, 8:182-191.
Kruk et al., "Nuclear spin relaxation in paramagnetic systems with zero-field splitting and arbitrary electron spin," Phys Chem Chem Phys 2001, 3:4907-4917.
Lauffer, R. S., "Paramagnetic Metal Complexes as Water Proton Relaxation Agents for NMR Imaging: Theory and Design," Chem Rev 1987, 87:901-927.
Li et al., "A Calcium-Sensitive Magnetic Resonance Imaging Contrast Agent," J Am Chem Soc 1999, 121:1413-1414.
Li et al., "Mechanistic Studies of a Calcium-Dependent MRI Contrast Agent," Inorg Chem 2002, 41:4018-4024.
Louie et al., "In vivo visualization of gene expression using magnetic resonance imaging," Nature Biotech 2000, 18:321-325.
Moats et al., "A 'Smart' Magnetic Resonance Imaging Agent that Reports on Specific Enzymatic Actvity," Angew Chem Int Ed Engl 1997, 36:726-728.
Qian et al., "Imaging f Zn2+ Release from Pancreatic beta-Cells at the Level of Single Exocytotic Events," Anal Chem 2003, 75:3468-3475.
Solomon, I, "Relaxation Processes in a System of Two Spins," Phys Rev 1955, 99(2):559-565.
Stefanidou et al., "Zinc: a multipurpose trace element," Arch Toxicol 2006, 80:1-9.

* cited by examiner

*Primary Examiner* — Noble Jarrell
(74) *Attorney, Agent, or Firm* — Casimir Jones, S.C.

(57) ABSTRACT

The present invention relates to contrast agents for magnetic resonance imaging (MRI). In particular, the present invention relates to MRI contrast agents that are activated in the presence of zinc(II) (e.g., resulting in a brighter image).

3 Claims, 6 Drawing Sheets

Scheme 1. Synthesis of 1. (a) Br(CH$_2$)$_3$OTBDMS, K$_2$CO$_3$, MeCN, 95%. (b) 1. Pd/C(10%), H$_2$, MeOH, 3 bar 2. tert-butylbromoacetate, Proton Sponge, NaI, MeCN, 92% (c) TBAF, THF, 90% (d) CBr$_4$, PPh$_3$, CH$_2$Cl$_2$, 47% (e) DO3A-tris-t-butyl ester, K$_2$CO$_3$, MeCN, 49%. (f) 1. TFA:TIPS:H$_2$O (95:2.5:2.5) 2. GdCl$_3$, pH ~7, 43%

ZINC-ACTIVATED CONTRAST AGENTS

The present application claims priority to U.S. Provisional Patent Application Ser. No. 60/839,722, filed Aug. 23, 2006, the disclosure of which is herein incorporated by reference in its entirety.

The development of the present invention was funded, in part, under NIH Grant 1RO1EB005866-01 and U.S. Army Medical Research and Materiel Command Grant 91008600DAMD17-02-1-0693. The government has certain rights in the invention.

FIELD OF THE INVENTION

The present invention relates to contrast agents for magnetic resonance imaging (MRI). In particular, the present invention relates to MRI contrast agents that are activated in the presence of zinc(II) (e.g., resulting in a brighter image).

BACKGROUND OF THE INVENTION

Magnetic Resonance Imaging (hereinafter "MRI") is a powerful imaging tool that produces results analogous to x-ray images without requiring the application of harmful radiation. The nuclei of many atoms have a property called spin, which is associated with a small magnetic moment. In the absence of an external magnetic field, the distribution of the orientations of these magnetic moments is random. In the presence of a static external magnetic field, the nuclear magnetic moments precess about the field direction, producing a net alignment in the field. MRI works by exciting the molecules of a target object using a harmless pulse of radiofrequency ("RF") energy to excite molecules that have first been aligned using a strong external magnetic field and then measuring the molecules rate of return to an equilibrium state within the magnetic field following termination of the RF pulse.

For example, in NMR imaging, a patient is placed in a static field and a short radio frequency pulse is applied via a coil surrounding the patient. The radio frequency or RF signal is selected for the specific nuclei (e.g. $^1H$) that are to be resonated. The RF pulse causes the magnetic moments of these nuclei to align with the new field and to precess in phase. On termination of the pulse, the moments return to the original distribution of alignments with respect to the static field and to a random distribution of precession phases, thereby giving off a nuclear magnetic resonance signal that can be picked up by a receiving coil. The NMR signal represents a proton density map of the tissue being studied.

Two additional values can be determined when the RF pulse is turned off and the nuclear magnetic moments are relaxing or returning to equilibrium orientations and phases. These are $T_1$ and $T_2$, the spin-lattice and spin-spin relaxation times. $T_1$ represents a time characteristic of the return to equilibrium spin distribution, equilibrium alignment of the nuclear magnetic moments in the static field. $T_2$, on the other hand, represents a time characteristic of the return to random precession phase distribution of the nuclear magnetic moments. Hence, the NMR signal that is generated may contain information on proton density, $T_1$ and $T_2$. The visually readable images that are generated as output are the result of computer data reconstruction on the basis of that information.

Because successful imaging depends on the ability of the computer to recognize and differentiate between different types of tissue, it is not uncommon to apply a contrast agent to the tissue prior to making the image. The contrast agent alters the response of the aligned protons to the RF signal. Good contrast agents interact differently with different types of tissue, with the result that the effect of the contrast agent is greater on certain body parts, thus making them easier to differentiate and image. Various contrast agents are known for various medical imaging techniques, including X-ray, magnetic resonance and ultrasound imaging. Magnetic resonance contrast agents generally function by modifying the density or the characteristic relaxation times $T_1$ and $T_2$ of the water protons, which results in resonance signals from which the images are generated.

Thus, a need exists for contrast agents having improved properties (e.g., in terms of contrast enhancement, water-solubility, biodistribution, stability, opacity, relaxivity, or tolerability).

DETAILED DESCRIPTION OF THE INVENTION

Figure 1:
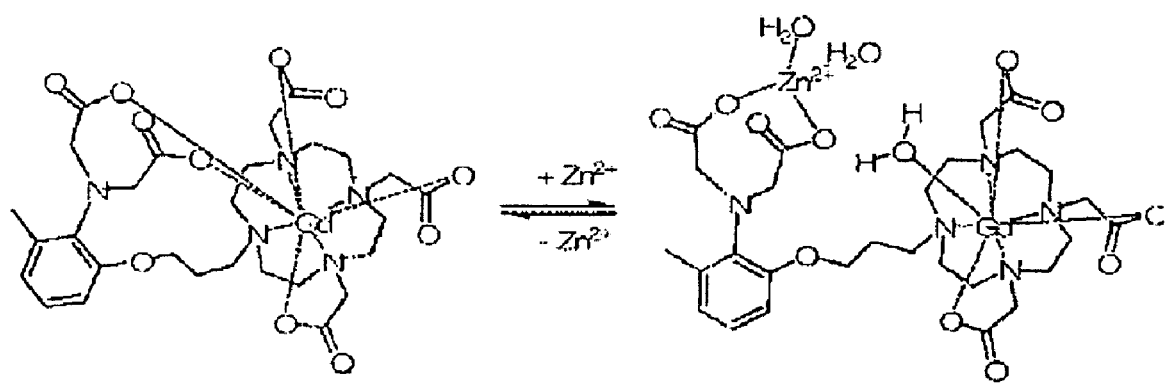
FIG. 1 shows a contrast agent with and without zinc and water binding.

The present invention relates to contrast agents for magnetic resonance imaging (MRI). In particular, the present invention relates to MRI contrast agents that are activated in the presence of zinc(II) (e.g., resulting in a brighter image).

Accordingly, the present invention provides MRI contrast agents that are activated in the presence of zinc(II) (e.g., resulting in a brighter image). The use of such an agent has many benefits including, but not limited to, the ability for deep tissue penetration and imaging of opaque organisms and tissues without sacrifice of the sample. In some embodiments, due to the change in the coordination environment surrounding gadolinium(III), an agent of the present invention produces a greater increase (e.g., greater than 50%, greater than 60%, greater than 70%, greater than 80%, greater than 90%, greater than 100%, or more) in relaxivity in the presence of zinc(II). In addition, in some embodiments, an agent of the present invention displays selectivity over magnesium(II) and calcium(II) and is, in some embodiments, reversible. Accordingly, agents and methods of the present invention find use in fields utilizing imaging (e.g., MRI), and are of valuable interest in the cellular imaging of zinc and also permits a better understanding of zinc distribution and its cellular activities.

Zinc(II) plays an important role in normal cellular function providing structural stability, catalytic activity, and acting as an ionic signal (1,2). Though the roles Zn(II) ions play in proteins have been elucidated, less is known about the mechanisms of its cellular actions and distribution. In particular, high concentrations of Zn(II) reside in neuronal synaptic vessels, up to 300 µMl (2), and in pancreatic β-islet cells (3). Release of this zinc has been implicated in a variety of pathological functions including the precipitation of β-amyloid seen in Alzheimer's patients (4,5). In light of these discoveries, there has been a large focus on the development of Zn(II) probes, principally fluorescent probes (6). A new and alternative approach provided by embodiments of the present invention is the development of MRI contrast agents as zinc sensors (e.g., the are able to sense the presence of zinc (e.g., thereby providing increased contrast and/or brighter images)). Unlike light-based microscopes, magnetic resonance imaging can provide three dimensional images without the problems of light scattering and photobleaching.

MRI takes advantage of the most abundant molecule in biological tissues: water. In the presence of a magnetic field, the magnetic moments of the protons in the water molecules orient themselves along the magnetic filed. An applied radiofrequency pulse inverts the magnetization vector and reorientation of the original magnetic filed direction occurs with a characteristic time constant. This process of realignment characterized by $T_1$ is called longitudinal or spin-lattice relaxation and it is the dominant factor in producing contrast in a $T_1$-weighted MR image. While intrinsic contrast between organs can be observed using MRI, resolution and sensitivity improves greatly with the use of contrast agents such as Gd(III) chelates. The efficacy of these complexes to decrease the $T_1$ of the local water protons, and therefore brighten the image, is measured by its relaxivity value ($mM^{-1}s^{-1}$)(7-9).

Recently, biologically active constrast agents have been developed in which a change in relaxivity is observed upon the involvement of the agent in a biological process (10-12). Variables that can contribute to the change in $T_1$ include the rotational correlation time ($\tau_R$), the exchange correlation time ($\tau_M$), and the number of bound water molecules of the metal center (q).

A calcium activated MRI contrast agent, GdDOPTA, (See, e.g., 12, 13) displays an increase in relaxivity due to modulation of (q) upon addition of calcium. In order to further characterize this agent, a series of ligands was generated during the development of embodiments of the present invention and were used to identify and characterize the role of the carboxylic acids that bind to either Gd(III) or Ca(II). In particular, the specificity of these ligands for several biologically prevalent dications was examined with a focus on Zn(II) binding.

Figure 2:
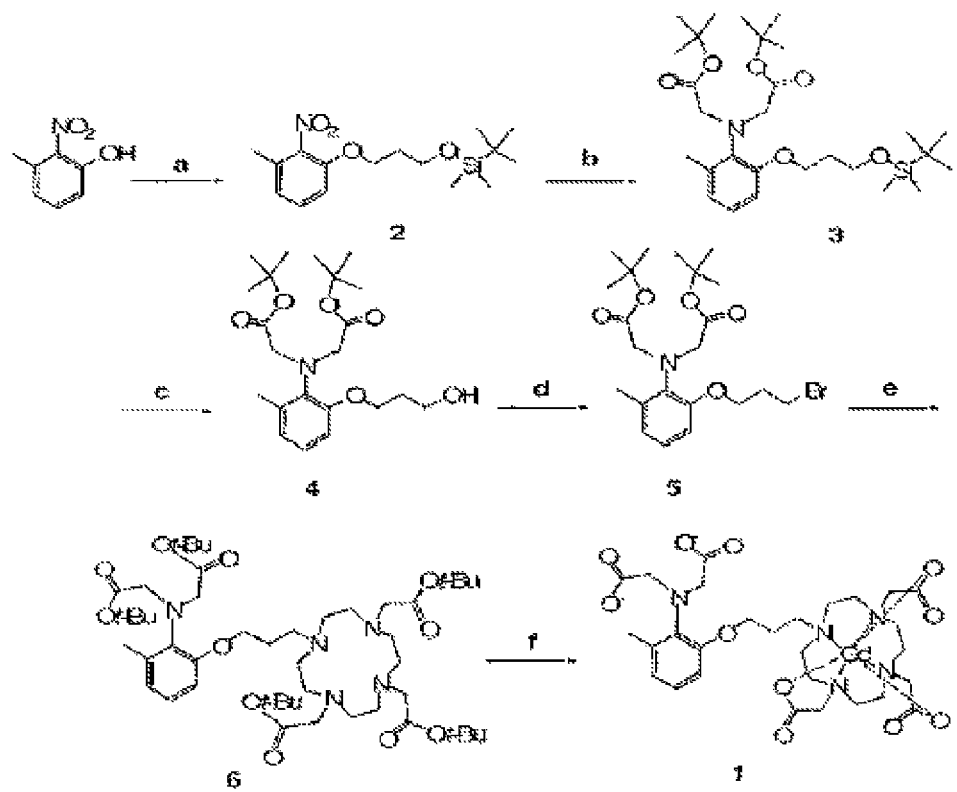
FIG. 2 shows a synthesis scheme for Compound 1

MRI contrast agents that are sensitive to Zn(II) concentrations have previously been developed based on the selective binding of Zn(II) to N,N,N',N'-tetrakis(2-pyridylmethyl)ethylenediamine(TPEN) (14, 15). Upon binding of Zn(II) to the pyridyl ligand, a conformational change is proposed to block water from the Gd(III) center and the consequent decrease in relaxivity results in a darker image. A more optimal approach would be to have a relative increase in relaxivity upon zinc binding to produce brighter images in the presence of zinc. Accordingly, the present invention provides a zinc-activated contrast agent, Compound 1 (See FIG. 2), that selectively and reversibly binds Zn(II) over Ca(II) and Mg(II). While Compound 1 is used to illustrate embodiments described herein, it should be understood that the present invention is not limited to the use of Compound 1. For example, compounds having the following structures are contemplated for use in the embodiments of the invention described herein.

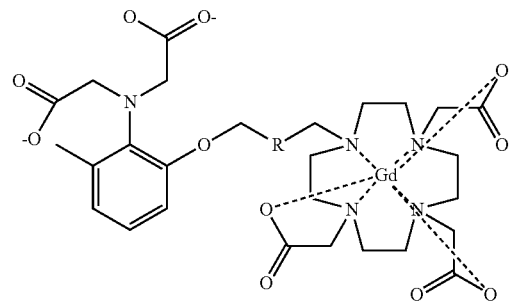

wherein $R=(CH_2)_n$(n=1 or 2). For example, the above compound, where n=2, was synthesized and tested and showed rapid detection of Zn(II) and high selectivity over Ca(II) and Mg(II), as well as detectability in the hundreds of micromolar range.

The binding is accompanied by a change in q similar to that observed for calcium binding to GdDOPTA (See FIG. 1). Thus, complex 1 provides a compound for which an increase in contrast is observed in the presence of Zn(II). Although an understanding of the mechanism is not necessary to practice the present invention and the present invention is not limited to any particular mechanism of action, in some embodiments, an increase in contrast in the presence of Zn(II) occurs through a change in gadolinium coordination upon binding Zn(II).

The synthesis of 1 (Scheme 1, See FIG. 2) begins with alkylation of the commercially available 3-methyl-2-nitrophenol to yield the protected alcohol product 2. The nitro group was reduced to the amine under standard palladium-catalyzed hydrogenation conditions and reacted immediately with tert-butylbromoacetate under basic conditions. 3 was reacted with tetrabutylammonium fluoride to deprotect the TBMDS group followed by bromination to give compound 5. DO3A-tris-t-butyl ester was synthesized following literature procedure (16) and combined with 5 to achieve the fully tent-butyl protection ligand, 6. After removal of the tert-butyl groups with TFA, the ligand was brought up in water and the pH adjusted to 6.5 with 1 M NaOH. $GdCl_3$ was added to the ligand while maintaining a steady pH for several days before precipitating any unreacted gadolinium with 1 M NaOH. The final metal complex, 1, was HPLC purified and verified by MS (17).

Figure 3:
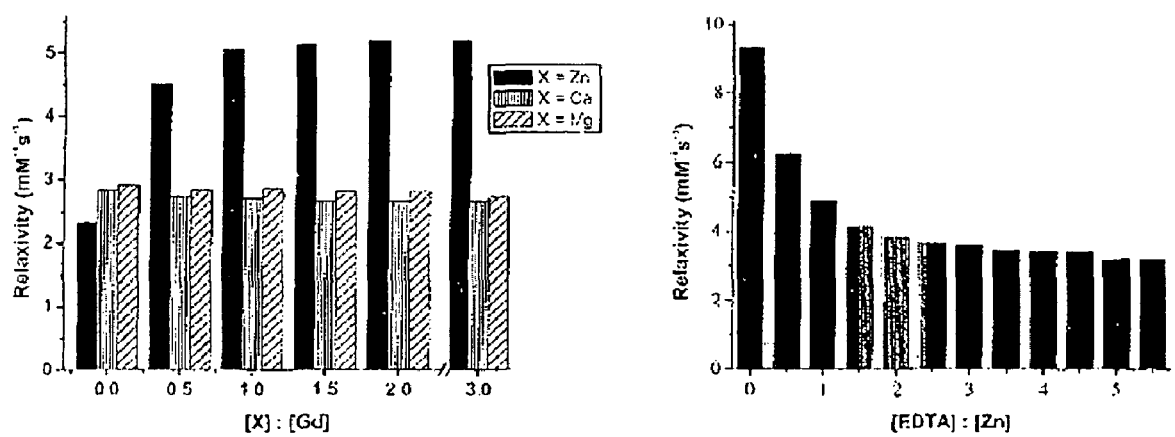
FIG. 3 shows relaxivity data. Left: Relaxivity of Compound 1 in the presence of $XCl_2$, where X=Zn, Ca, and Mg. All solutions were made in 100 mM KCl/100 mM HEPES at ph=7.4. Right: Relaxivity of Zn-1, 3:1 (Zn:Gd), following titration of EDTA.

To test the binding ability of the acetate ligands to Zn(II), relaxivity measurements of 1 were measured in the absence and presence of $ZnCl_2$. The relaxivity of 1 in HEPES buffer without zinc was 2.34 $mM^{-1}$ $s^{-1}$, as is typical for small molecule contrast agents for which q=0 (8). This result indicates that water is blocked from the gadolinium center by the acetate ligands. As $ZnCl_2$ was added, the relaxivity increased to 5.3 $mM^{-1}$ $s^{-1}$ indicative of a q=1 complex (See FIG. 3, left). Similar studies were conducted using $MgCl_2$ and $CaCl_2$ to test for selectivity of the ligand for zinc over other dications known to have higher cellular concentrations and which have similar binding affinities for carboxylic acids. There was no significant change in relaxivity values for either Mg(II) or Ca(II) even when a 3-fold excess of the dication was present (See FIG. 3, left). A competitive binding assay gave a dissociation constant of $2.38 \times 10^{-4}$ M for the Gd(III)-Zn(II) complex. In vitro MR images confirm that hundreds of micromolar levels Zn(II) can be detected using this contrast agent.

After 1 was left to equilibrate at 37° C. for 3 days with an excess of zinc, a relaxivity of 9.2 $mM^{-1}$ $s^{-1}$ was measured, indicating the species has a value of q=2. This measurement corresponds well to a structure proposed by embodiments of the present invention in which the pendant ligands have left the gadolinium for the zinc, leaving two open coordination sites for water to bind. When the Zn-1 samples are titrated with EDTA, the relaxivity decreases to the original values. Although an understanding of the mechanism is not necessary to practice the present invention and the present invention is not limited to any particular mechanism of action, in some embodiments, this is due to sequestration of Zn(II) by EDTA which leaves the carboxylic acids available to bind to Gd(III) and close the coordination sites (See FIG. 3, right). Adding excess EDTA had no effect on the relaxivity, providing that the Gd(III) ions are not sequestered by EDTA as expected given the high binding constant (~$10^{16}$) for Gd-EDTA for which q=1.

Figure 4:
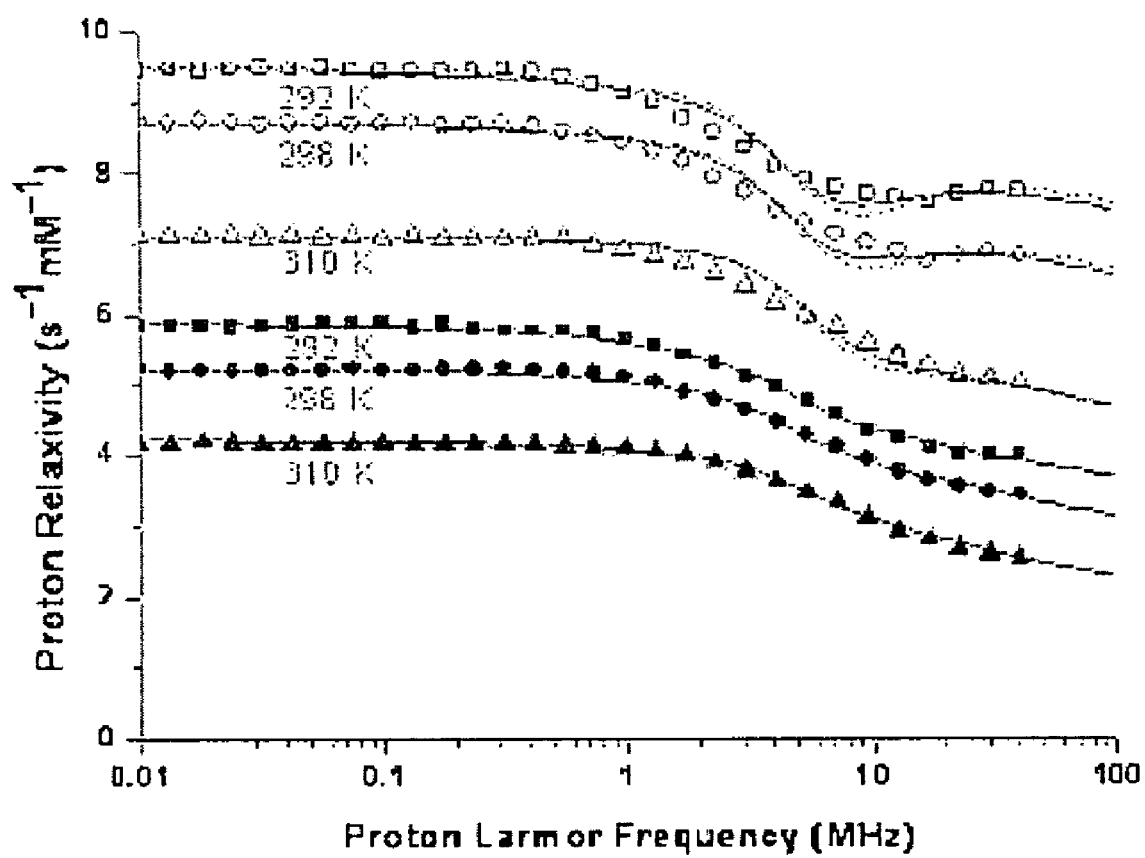
FIG. 4 shows water proton relaxivity data for Compound 1 in the absence (solid symbols) and in the presence (open symbols) of Zn(II) at varying temperatures (squares=292 K, circles=298 K, and triangles=310K). The solid and dashed lines are best fit curves to approximate theories for i) fast rotating complexes in the absence of static ZFS or ii) slow rotating complexes in the presence of static ZFS, respectively.

The nuclear magnetic relaxation dispersion (NMRD) profiles of Compound 1, measured in the presence and absence of Zn(II) at 292°, 298° and 310° K., are reported in FIG. 4. The observed bulk water proton relaxivity is provided by the sum of i) the outer-sphere contribution, due to the dipolar interaction between unpaired electrons and protons of freely diffusing water molecules, and ii) the inner-sphere contribution. The latter is due to the dipolar interaction between unpaired electrons and protons of water molecules coordinated to the paramagnetic ion (first sphere) or anchored at a fixed distance r from the metal ion (second-sphere) in exchange with bulk water protons. When such exchange is fast (i.e. the exchange rate is faster than the relaxation rate of the protons of bound water molecules), the observed bulk water proton relaxivity is a good reporter of the presence of water molecules coordinated to the metal ion. A slow exchange regime, on the other hand, is characterized by an increase in relaxivity with increasing temperature, as the exchange rate increases with temperature.

An overall increase in relaxivity is observed at all fields in the Zn(II)-containing sample. Such increase is in agreement with a larger hydration of the gadolinium site. The decrease in relaxivity with increasing temperature actually indicates the occurrence of a fast exchange regime for the inner-sphere relaxation. Outer-sphere relaxation is always expected to decrease with increasing temperature. One dispersion is present in all profiles, at about 2-10 MHz, as expected for both the outer-sphere relaxation and the inner-sphere relaxation for complexes with reorientational times of the order of 100 ps, in agreement with the molecular weight of the present system, and electron relaxation times typical of gadolinium complexes. The increase in relaxivity at high frequencies, observed for the profiles of the Zn(II)-containing sample acquired at the lower temperatures, indicates the field dependence of the electron relaxation time.

The analysis performed according to current theories (Bertini, I., Luchinat, C. & Parigi, G. (2005) in Relaxometry of water-metal ion interactions, eds. Bertini, I. & van Eldik, R., Vol. 57, pp. 105-172) confirms that in the absence of Zn(II), the outer-sphere contribution is dominant, setting an upper limit for the possible fraction of coordinated water q=0.3±0.2, calculated for water protons at a typical distance for the first-coordination sphere of Gd(III) (~3.1 Å). The relaxation rates can be very well reproduced using the Freed model (Hwang, L. P. & Freed, J. H. (1975) *J Chem Phys* 63, 4017-4025) and the Solomon-Bloembergen-Morgan (SBM) theory (Solomon, I. (1955) *Phys. Rev.* 99, 559-565; Bloembergen, N. & Morgan, L. O. (1961) *J. Chem. Phys.* 34, 842-850) and second-sphere relaxation (solid lines in FIG. 4). The latter is due to the presence of two water protons at 3.7 Å from the metal ion with a field dependence for the electron relaxation rates similar to what is obtained for Gd-DTPA.

The overall increase in the relaxation rate values obtained for the Zn(II)-coordinated complex (open symbols in FIG. 4) can be reproduced with SBM theory considering the presence of an additional regularly coordinated water molecule: a q=1.2±0.3 is in fact obtained. The best fit profiles (solid lines in FIG. 4) are satisfactory although not always in perfect agreement with the experimental data, probably due to the presence of both static and transient zero field splitting (ZFS), as expected for Gd(III) complexes. Presently, available fitting programs cannot properly account for their simultaneous presence in fast rotating systems. The SBM theory in fact neglects the presence of static ZFS. Data were also analyzed using a slow rotation program including ZFS (Bertin, I., Kowalewsi, J., Luchinat, C., Nilsson, T. & Parigi, G. (1999) *J. Chem. Phys.* 111, 5795-5807; Kruk, D., Nilsson, T. & Kowalewsi, J. (2001) *Phys. Chem. Chem. Phys.* 3, 4907-4917). Even in such model, the data are consistent with the presence of a regularly coordinated water molecule (dotted lines in FIG. 4). These results indicate that a water molecule in fast exchange is regularly coordinated to the Gd(III) ion in the presence of Zn(II), whereas it is not detected in the absence of Zn(II), in agreement with the scheme depicted in FIG. 1.

Proton relaxivity measurements on Compound 1 were also performed while titrating with increasing amounts of Zn(II) up to 1:1.4 (Gd: Zn) equivalents. The titration showed a linear increase in the observed relaxation rate enhancement until 1:0.8 (Gd:Zn) equivalents, and then the latter leveled to a plateau at 1.2-1.4 equivalents. This confirms that a 1:1 (Gd: Zn) complex is formed, as relaxivity did not increase when Zn(II) was added in excess. The observed linear dependence also rules out the possibility of a 2:1 (Gd:Zn) complex formation.

Figure 5:
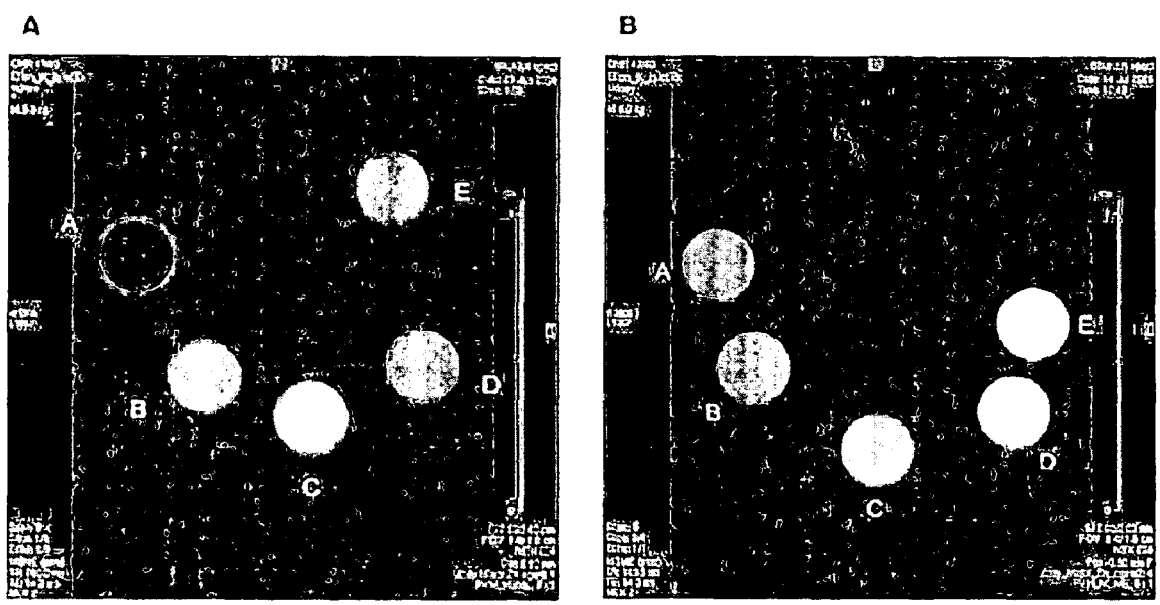
FIG. 5 shows T1-weighted phantom MR images. A. Compound 1 selectivity. Images of a 1 mM solution of Compound 1 in HEPES buffer. (A) HEPES buffer only; (B) Compound 1; (C) Compound 1 with 1 mM ZnCl2; (D) Compound 1 with 1 mM MgCl2; (E) Compound 1 with 1 mM $CaCl_2$. B. Compound 1 sensitivity. Images of a 1 mM solution of Compound 1 in HEPES buffer with varying zinc concentrations. (A) 0 μM Zn; (B) 50 μM Zn; (C) 100 μM Zn; (D) 500 μM Zn; (E) 1 mM Zn. (TR=100.0 ms, TE=14.3 ms, FOV=2.5/2.0 cm, data matrix=256×256. TR=repetition time; TE=echo time; FOV=field of view).

To evaluate the effectiveness of Compound 1 as an in vivo probe, the stability of Zn-Compound 1 was investigated. Using the commercially available fluorophore FluoZinTM-1 (Invitrogen), the binding constant of zinc can be determined by a competitive assay. Since the Zn(II)-binding regions of the dye and Compound 1 are identical, similar binding constants are to be expected. Using the published dissociation constant for the dye (8.6×10-6 M) the Kd of Zn-Compound 1 was calculated to be $2.4 \times 10^{-4}$ M. Compound 1 is sensitive enough to bind Zn(II) in the hundreds of micromolar concentration range allowing one to investigate MR imaging of Zn(II) release in the brain. In vitro MR images of a 4.7 T magnet show an increase in intensity for Compound 1 in the presence of Zn(II) while there is no discernible difference of Compound 1 with Ca(II) or Mg(II) (FIG. 5A). More importantly, phantom images of various Zn(II) concentrations shows that one can easily visualize the difference between 100 μM and 500 μM zinc concentrations (FIG. 5B). To confirm there was a measurable difference between zinc concentrations, T1 was measured on these same samples on a 14.1 T magnet and on a 1.4 T magnet.

Compound 1 was monitored for 24 hours in a 0.1 M phosphate buffer to determine its stability in solution. Due to the low solubility of $GdPO_4$ (Ksp=$10^{-22.26}$ mol$^2$/L$^2$) any dissociation of gadolinium from Compound 1 will precipitate, causing a subsequent decrease in relaxivity which was not seen. A more accurate measurement of the amount of gadolinium dissociation can be made from centrifuging the samples and collecting aliquots of the supernatant for evaluation of gadolinium concentration via ICP. This was done at various time-points up to 24 hours and it was found that there was no significant change in [Gd], indicating no loss of gadolinium from the Compound 1 complex. This suggests a dissociation constant for Compound 1 on the order of that seen for Gd-DO3A (log Kd=21) and its derivatives.

Figure 6:
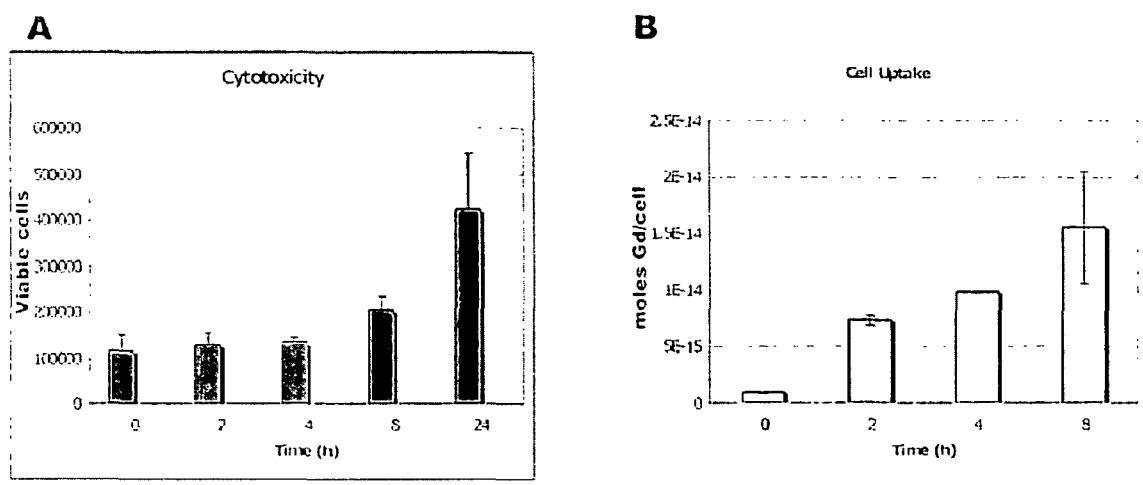
FIG. 6 shows cell cytotoxicity and uptake of 0.5 M Compound 1 with NIH/3T3 cells. A. Normal proliferation of NIH/3T3 cells is seen when incubated with 0.5 M Compound 1. The cell doubling time for NIH/3T3 cells is around 16 hours and one can see over twice as many cells at 24 hours than at 8 hours as one would expect, implying greater than 99% cell viability. B. Compound 1 is taken up at a constant rate for up to 8 hours.

Treatment of NIH/3T3 cells with 0.5 mM Compound 1 for up to 24 hours shows no observable cell death as visualized by trypan blue staining Cells proliferated exponentially at the expected rate indicating low toxicity affects from the agent (FIG. 6A). Compound 1 was effectively taken up by NIH/3T3 cells at a constant rate for the first 8 hours of treatment. The maximal intracellular concentration of Compound 1 of approximately $10^{-14}$ mol Gd/cell is achieved at 8 hours and maintained up to 24 hours (FIG. 6 B). NIH/3T3 cells were seeded at $10^5$ cells per well in 24-well tissue culture plates with Dulbecco's modified Eagle's medium (DMEM) containing 10% bovine calf serum and incubated overnight in a 5% $CO_2$ incubator at 37° C. The media was then changed and Compound 1 added at a concentration of 500 µM. After 2, 4, 8, and 24 hours, cells were washed three times with 1×PBS and exposed to 250 µL of 0.25% trypsin and harvested. Cells were diluted with an equal volume of 0.4% trypan blue and counted on a hemacytometer. For cellular uptake of Compound 1 into cells, cells were incubated with concentrated nitric acid at 70° C. for 3 hours. The dissolved cells were diluted into a 5 ml, solution with 3% nitric acid and 5 ppb of an indium internal standard. The concentration of Gd(III) was then determined using ICP-MS (induction coupled plasma mass spectrometry).

A second agent, with only two methylenes linking the gadolinium chelate with the zinc-binding aminoacetates was synthesized and tested but showed little activation towards Zn(II).

With over a 100% increase in relaxivity, and a binding constant in the hundreds of micromolar range, Compound 1 is contemplated to have the ability to visualize changes in Zn(II) concentrations in extracellular fluids of the brain. The release of high concentrations of Zn(II) (200-300 µM) from neuronal synaptic vessels into the extracellular fluids of the brain (~10 nM) when under stress has been implicated in a variety of pathological functions including the precipitation of β-amyloid plaques seen in Alzheimer's disease. Thus, the compositions and methods of the present invention provide for the ability to detect, diagnose, characterize, and analyze a variety of neurological conditions and statuses.

The compounds of the invention may be provided in pharmaceutical form and/or in kits. For example, in some embodiments, the compounds, or salts thereof, are provided with one or more pharmaceutically acceptable adjuvants, excipients or diluents for use in enhancing image contrast in in vivo imaging or for treatment of a disease. Methods of manufacturing the compounds and/or compositions containing the compounds are provided. In some embodiments, the present invention provide use of a compound in the preparation of a contrast medium for use in a method of diagnosis involving administering the contrast medium to a human or animal body and generating an image of at least part of the body. In some embodiments, the compositions and methods employ two or more different contrast agents.

Cite references (herein incorporated by reference in their entireties).

[1] M. Stefanidou, C. Maravelias, A. Dona, C. Spiliopoulous, *Archives of Toxicology* 2006, 80, 1.
[2] C. J. Frederickson, J-Y Kob, A. I. Bush, *Nature Reviews. Neuroscience* 2005, 6, 449.
[3] W.-J. Qian, K. R. Gee, R. T. Kennedy, *Analytical Chemistry* 2003, 75, 3468.
[4] C. J. Frederickson, M. P. Cuajungco, C. J. Frederickson, *Journal of Alzheimer's Disease* 2205, 8, 155.
[5] A. I. Bush, *TRENDS in Neurosciences* 2003, 26, 207.
[6] K. Kikuchi, K. Komatsu, T. Nagano, *Current Opinion in Chemical Biology* 2004, 8, 182.
[7] A. Merbach, E. Toth, *The Chemistry of Contrast Agents in Medical Magnetic Resonance Imaging*, John Wiley & Sons, Ltd., New Yolk, 2001.
[8] P. Caravan, J. J. Ellison, T. J. McMurry, R. B. Laufer, *Chem. Rev.* 1999, 99, 2293.
[9] R. B. Lauffer, *Chem. Rev* 1987, 87, 901.
[10] R. A. Moats, S. E. Fraser, T. J. Meade, *Agnew Chem. Int. Ed Engl.* 1997, 36, 726.
[11] A. Y. Louie, M. M. Huber, E. T. Ahrens, U. Rothbacher, R. Moats, R. E. Jacobs, S. E. Fraser, T. J. Meade, *Nature Biotechnology* 2000, 18, 321.
[12] W.-H. Li, S. E. Fraser, T. J. Meade, *JACS* 1999, 121, 1413.
[13] W.-H. Li, G. Parigi, M. Fragai, C. Luchinat, T. J. Meade, *Inorganic Chemistry* 2002, 41, 4018.
[14] K. Hanaoka, K. Kikuchi, Y. Urano, T. Nagano, *Journal of Chrmical Society, Perkin Transactions* 2 2001, LOOK UP, 1840.
[15] K. Hanaoka, K. Kikuchi, Y. Urano, M. Narazaki, D. Yokawa, S. Sakamoto, K. Yamaguchi, T. Nagano, *Chemistry & Biology* 2002, 9, 1027.
[16] A Dadabhoy, S. Faulkner, P. G. Sammes, *J. Chem. Soc., Perkin Trans.* 2 2002, 348.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A zinc activated contrast agent that selectively binds Zn(II) over Ca(II) and Mg(II), wherein said contrast agent displays an increase in relaxivity upon zinc binding, and wherein said agent is:

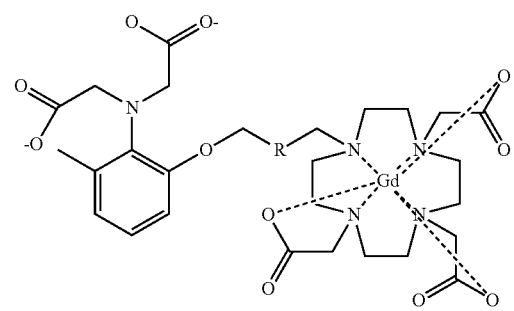

wherein R=$(CH_2)_n$(n=1 or 2).

2. A method for magnetic resonance imaging comprising:
a) treating a biological sample with a zinc activated contrast agent that selectively binds Zn(II) over Ca(II) and Mg(II), wherein said contrast agent displays an increase in relaxivity upon zinc binding and brighter images in the presence of zinc, wherein said agent is and
b) detecting signal.

3. The zinc activated contrast agent of claim 2, wherein said agent reversibly binds Zn(II).

* * * * *

UNITED STATES PATENT AND TRADEMARK OFFICE
CERTIFICATE OF CORRECTION

| | | |
|---|---|---|
| PATENT NO. | : 7,906,105 B1 | Page 1 of 1 |
| APPLICATION NO. | : 11/844088 | |
| DATED | : March 15, 2011 | |
| INVENTOR(S) | : Jody L. Major and Thomas J. Meade | |

It is certified that error appears in the above-identified patent and that said Letters Patent is hereby corrected as shown below:

Column 1, lines 7-11 should read, --This invention was made with government support under Grant No. 1 R01 EB005866-01 awarded by the National Institutes of Health and Grant No. DAMD17-02-1-0693 awarded by the U.S. Army Medical Research and Material Command (through a Subcontract from Wayne State University, Subcontract Number WSU 02044). The government has certain rights in the invention.--

Column 8, Claim 2, lines 60-61 should read, --the presence of zinc, wherein said agent is:

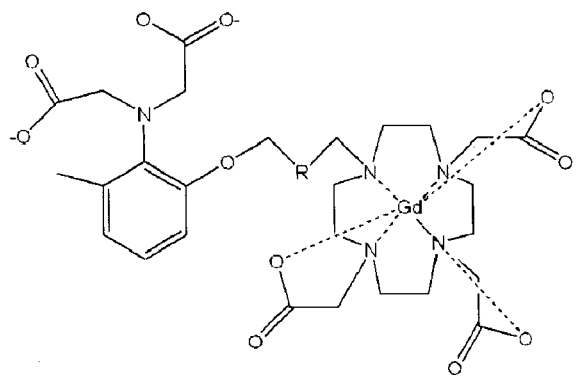

wherein $R=(CH_2)_n$ (n=1 or 2); and--

Signed and Sealed this
Sixteenth Day of August, 2011

David J. Kappos
*Director of the United States Patent and Trademark Office*